United States Patent [19]

Birkle et al.

[11] Patent Number: 5,040,090
[45] Date of Patent: Aug. 13, 1991

[54] CAPACITIVE MOISTURE-SENSOR

[75] Inventors: Siegfried Birkle, Hoechstadt/Aisch; Johann Kammermaier, Unterhaching; Albert Hammerschmidt; Gerhard Rittmayer, both of Erlangen; Hellmut Ahne, Roettenbach, all of Fed. Rep. of Germany

[73] Assignee: Siemens Aktiengesellschaft, Berlin & Munich, Fed. Rep. of Germany

[21] Appl. No.: 514,607

[22] Filed: Apr. 26, 1990

[30] Foreign Application Priority Data

May 2, 1989 [DE] Fed. Rep. of Germany ....... 3914519

[51] Int. Cl.$^5$ .............................................. H01G 5/20
[52] U.S. Cl. .................... 361/286; 29/592.1
[58] Field of Search ............... 73/336.5; 361/286; 29/592; 430/322, 326, 330

[56] References Cited

U.S. PATENT DOCUMENTS

| 4,164,868 | 8/1979 | Suntola | 73/336.5 |
| 4,305,112 | 12/1981 | Heywang et al. | 361/286 |
| 4,339,521 | 7/1982 | Ahne et al. | 430/192 |
| 4,395,482 | 7/1983 | Ahne et al. | 430/326 |
| 4,619,500 | 10/1986 | Ahne et al. | 350/341 |
| 4,622,285 | 11/1986 | Ahne | 430/322 |
| 4,761,710 | 8/1988 | Chen | 361/286 |
| 4,849,051 | 7/1989 | Ahne et al. | 156/659.1 |
| 4,965,134 | 10/1990 | Ahne et al. | 428/411.1 |

FOREIGN PATENT DOCUMENTS 300575 1/1989 European Pat. Off. .
3716629 12/1988 Fed. Rep. of Germany .
2149922 6/1985 United Kingdom .

OTHER PUBLICATIONS

"Proc. 3rd Int. Conf. Solid-State Sensors and Actuators (Transducers '85) Jun. 11-14, 1985", pp. 210-220.
"Sensors and Actuators", vol. 13 (1988), pp. 243-250.
"IEEE Transactions on Components, Hybrids, and Manufacturing Technology", vol. CHMT-2 (1979), No. 3, pp. 321-323.
"Sensors and Actuators", vol. 8 (1985), pp. 23-28.
"Sensors and Actuators", vol. 12 (1987), pp. 291-296.
K. Carr-Brion, "Moisture Sensors in Process Control", Elsvier Applied Science Publishers, London and New York, 1986, pp. 22-24.
Erich Behr "Hochtemperaturbestandige Kunststoffe Mit 93 Bildern und 32 Talbellen".

Primary Examiner—Donald A. Griffin
Attorney, Agent, or Firm—Kenyon & Kenyon

[57] ABSTRACT

A capacitive moisture sensor with a dielectric consisting of a moisture sensitive polymer which is mounted between two electrodes fulfills all the requirements of capacitive moisture sensors to a high degree, in particular with regard to a high long-term stability, when the organic polymer is a polybenzoxazole or a polybenzothiazole.

13 Claims, No Drawings

CAPACITIVE MOISTURE-SENSOR

BACKGROUND OF THE INVENTION

1. Field of the Invention

The invention relates to a capacitive moisture sensor with a dielectric comprising a moisture-sensitive organic polymer which is mounted between two electrodes. The invention also relates to a method of preparing this type of a capacitive moisture sensor.

2. Description of Related Art

The detection or determination of moisture in gases, in particular in the air, plays an important role in all air-conditioning matters, such as in air-conditioning buildings as well as in refrigeration or green houses, and in dehumidifying processes. Reproducible operating moisture sensors or detecting devices, which should be cost effective, should guarantee energy-saving air conditioning or dehumidification in connection with a corresponding, automatic measuring and control system.

Capacitive moisture sensors, in which the relative changes in capacitance ΔC/C steadily increase with the amount of water absorbed in the dielectric and therefore also serve as moisture measuring parameters, are particularly suited for measuring the relative atmospheric humidity, which is important for processing techniques. In connection with this, the moisture sensors must have a series of important properties, namely quick response time, little or no temperature sensitivity, no long-term drift, insensitivity to flowing gases, resistance to corrosion in particular to aggressive media, and low cross-sensitivity in particular to organic solvents Moreover, the sensors must deliver electronically measurable signals which are able to be processed in a simple manner by modern microcomputer systems. For reasons of circuit engineering, a linear correlation between the absorbed moisture and the sensor signal is advantageous.

Cost effective, capacitive moisture sensors can be realized e.g. with thin, water-permeable metal electrodes and a moisture sensitive or responsive organic polymer, whose dielectric constant changes characteristically with the absorbed moisture. Such a moisture sensor is known e.g. from DE-OS 28 48 034. The advantages of moisture sensors of the said type are above all a measurement, i.e., moisture determination, which is independent from the flow rate of the surrounding medium; a uniform measuring responsiveness; a low maintenance cost; and a quick response rate (c.f. e.g.: K. Carr-Brion, "Moisture sensors in Process Control", Elsevier Applied Science Publishers, London and New York, 1986, pp 22 to 24). Incidentally, in addition to the moisture-dependent measurement of changes of capacitance (also c.f.: "Sensors and Actuators", Vol. 12 (1987), pp 291 to 296, as well as: U.S. Pat. No. 4,164,868), measurements of the electrical resistance can also be drawn upon as a measure for the relative atmospheric humidity (c.f. "Sensors and Actuators", Vol. 8 (1985), pp 23 to 28, as well as: "Proc. 3rd Int. Conf. Solid-State Sensors and Actuators (Transducers '85), June 14–15, 1985", pp 210 to 212) and changes in impedance (c.f.: "Sensors and Actuators", Vol. 13 (1988), pp 243 to 250).

Various materials are already known as moisturesensitive polymers for moisture sensors, e.g.: cellulose acetate butyrate ("IEEE Transactions on Components, Hybrids, and Manufacturing Technology", Vol. CHMT-2 (1979), No. 3, pp 321 to 323, as well as: "Sensors and Actuators", Vol. 12 (1987), pp 291 to 296);

polyimide ("Proc. 3rd Int. Conf. Solid-State Sensors and Actuators (Transducers ,85), June 11–14, 1985", pp 217 to 220);

cross-linked copolymers of styrene sulfonate and polyvinylchloride ("Sensors and Actuators", Vol. 8 (1985), pp 23 to 28);

copolymers of ionic monomers, like the sodium salt from styrene-4-sulfonic acid and methacrylic acid, or non-ionic monomers like styrol and (meth)acrylic acid methylester ("Proc. 3rd Int. Conf. Solid-State Sensors and Actuators (Transducers ,85), June 11–14, 1985" pp 210 to 212);

graft copolymers of polytetrafluoroethylene and styrene or 4-vinylpyridine with acid or alkaline groups ("Proc. 3rd Int. Conf. Solid-State Sensors and Actuators (Transducers '85), June 11–14, 1985" pp 213 to 216); and quaternized 4-vinylpyridine styrene copolymers and poly-4-vinylpyridine which is partially quaternized or crosslinked with dibromobutane ("Sensors and Actuators", Vol. 13 (1988), pp 243 to 250).

The primary disadvantages of moisture sensors with polymer materials of the aforesaid type are a limited measuring range, a strong temperature sensitivity, the appearance of hysteresis and poor long-term stability. Moreover, these types of materials are often accessable only as foils, whose available thickness does not permit a desirable, quick response time.

It is an object of the invention to provide a capacitive moisture sensor of the aforesaid type with a dielectric comprising a moisture sensitive organic polymer between a pair of electrodes.

It is a further object of the invention to provide such a capacitive moisture sensor which has a high, long-term stability and which fulfills all the requirements of such sensors to a high degree.

It is a further object of the invention to provide such a capacitive moisture sensor wherein the least possible amount of long-term drift results and wherein a structuring of the dielectric should be possible.

SUMMARY OF THE INVENTION

In accordance with the invention, the foregoing objects are achieved by providing a capacitive moisture sensor having a dielectric comprising a moisture sensitive organic polymer which is a polybenzoxazole or a polybenzothiazole between a pair of electrodes.

DETAILED DESCRIPTION OF THE INVENTION

Polybenzoxazoles and polybenzothiazoles are high-temperature stable polymers. Layers of these types of polymers have properties which make them particularly suited for use as a dielectric in capacitive moisture sensors. These properties are in particular:

A substantial linear correlation between the relative humidity (r.F.) and the change of the dielectric constant ($\epsilon$ r);

the size of the change: approx. 30% change of $\epsilon r$ between 0 and 100% r.F., allowing the use of simple circuits;

the low response to temperature changes: approx. 15% change of $\epsilon r$ between 30° and 9° C. at 100% r.F., permitting a simple adjustment of temperature;

a good reproducibility (no change of $\epsilon r$ after a few cycles); and excellent long-term stability, even at high atmospheric humidity.

In the case of the moisture sensor according to the invention, both of the electrodes are advantageously of a flat design. Since the dielectric mounted between the electrodes is covered by them, at least one of the two electrodes must be moisture permeable. The electrodes can, however, also be designed in e.g. a comb shape. In this case, a direct access of the moisture to the dielectric is possible. Both of the electrodes can also be mounted at a distance from each other on a substrate. In this case, the dielectric is located on the substrate in the space between the two electrodes. The electrodes usually consist of metal.

The capacitive moisture sensor according to the invention is advantageously prepared in a way such that a polybenzoxazole or polybenzothiazole precursor, which represents a prepolymer, is applied in the form of a layer or foil to an electrically conductive layer. This is then subsequently annealed, whereby a layer of polybenzoxazole or polybenzothiazole develops, that is, the polymer precursor is converted into the appropriate polymer. The polybenzoxazole or polybenzothiazole layer is subsequently provided with a second electrically-conductive layer. Since both of the conductive layers, which generally consist of metal, serve as electrodes in the finished moisture sensor, at least one of these layers must be moisture permeable.

In comparison to the materials which are currently being used, the polybenzoxazoles and polybenzothiazoles, which are used as a dielectric in the moisture sensor according to the invention, have the advantage that they can be photostructured in polymer precursor form. This makes possible a rational processing using modern techniques typical of microelectronic engineering, such as micro structuring. The structuring of the polymer precursors can take place e.g. by means of laser beams. Preferably, however, a photoactive component is added to the polybenzoxazole or polybenzothiazole precursor, and the layer or foil consisting of the polymer precursor is then photostructured before annealing. The structuring or processing thereby takes place as in the case of conventional positive resists. Such a procedure makes possible the preparation of very thin, pinhole free layers (thickness: approx. 0.5 μm), which is favorable for the response time of the moisture sensor. Furthermore, new techniques, such as microstructuring, can be used for cost efficient, rational production methods, which, e.g., permits the design of chip-integrated moisture sensors.

Light-sensitive diazoquinones, in particular o-quinone diazides and o-naphthoquinone diazides, can be used as photoactive constituents. These types of photoactive constituents are known e.g. from the following publications: EP-OS 0 023 662, EP-OS 0 291 779 and DE-OS 37 16 629. Polybenzoxazole precursors, which can be used to prepare the moisture sensor according to the invention, are also known from these publications. Polybenzothiazole precursors are known e.g. from DE-OS 34 11 659 and—as is equally the case with polybenzoxazole precursors—from E. Behr, "Hochtemperaturbestndige Kunststoffe" (High-Temperature Resistant Plastics), Carl Hanser Verlag, Munich 1969 (c.f. pp 99 to 102).

The polymer precursors are advantageously applied as a solution in an organic solvent to the electrically conductive layer or to the electrode. N-methylpyrrolidone is preferably used as a solvent. In addition, however, other organic solvents having similar properties, such as dimethyl formamide and N.N-dimethyl acetamide, as well as mixtures of the said solvents, can also be used.

The solution is preferably applied to the electrically conductive layer or electrode by means of a centrifugal technique. Other possible coating methods are dipping, spraying, brushing and rolling. After applying the solution to the conductive layer or electrode, the solvent is removed; i.e., it is dried. This can take place at room temperature or at an increased temperature, whereby it can also be done in a vacuum. It is subsequently annealed. The annealing preferably takes place at temperatures between 300° and 500° C.

For the purpose of photostructuring, the layers or foils of polymer precursors, which contain a photoactive constituent, are exposed to actinic light through a mask before annealing, by means of e.g. a super pressure mercury vapor lamp or are irradiated by guiding a corresponding light beam, electron beam or ion beam. The layers of foil parts which were exposed to light or were irradiated are subsequently dissolved out or drawn off.

The invention shall be more closely explained in light of the following exemplified embodiments.

EXAMPLE 1

Preparation of the Polymer Layer or of the Dielectric 5 g of a soluble polybenzoxazole precursor in the form of a hydroxypolyamide, which was prepared by polycondensation from 50 Mol-% 3.3'-dihydroxy benzidine, 50 Mol-% 2.2-Bis(3-amino-4-hydroxyphenyl)-1.1.1.3.3.3-hexafluoropropane and 90 Mol-% isophthalic acid dichloride (c.f.: "Polymer Letters", Vol. 2 (1964), pp 655 to 659), together with a photoactive constituent in the form of a naphthoquinone diazide prepared from Bisphenol A and diazo naphthoquinone-5-sulfonic acid chloride (c.f.: DE-OS 26 31 535) are dissolved in 10 g N-methylpyrrolidone. The solution is then pressurefiltered through a 0.8 μm filter. The photoresist solution obtained from this is centrifugally applied (1500 rpm, 20 sec.) to a silicon wafer provided with a Cr/Ni layer, and this is subsequently dried (forced- air oven, 90° C.). For contacting the Cr/Ni layer, the photoresist layer is carefully removed in two places using a suitable solvent such as N-methylpyrrolidone. This silicon wafer is subsequently annealed in the diffusion oven under nitrogen as an inert gas, whereby the following temperature program is run through: 1 hour to 170° C., 1 hour to 300° C., 1 hour to 400° C., 0.5 hours at 400° C., 3 to 4 hours to room temperature. A high-temperature resistant polybenzoxazole is developed in this manner.

EXAMPLE 2

Preparation of the Capacitive Moisture Sensor

A gold electrode is deposited by sputtering onto a polybenzoxazole layer prepared according to example 1 (surface resistance $R_\square = 10$ to $20\Omega$). Thin silver wires for contacting are attached with the aid of conductive glue to the bottom Cr/Ni electrode and to the top gold electrode, which is moisture permeable.

EXAMPLE 3

Measuring the Moisture Properties

Before measuring, the silicon wafer or the moisture sensor is conditioned at a temperature of 30° C. for two days at 100% r.F. The electric properties are subsequently measured at defined temperatures, i.e., at 30°, 60° and 95° C., between 0 and 100% r.F. The relative change in capacitance $\gamma = \Delta C/C$ (i.e. $C_{moist} - C_{dry}/C_{dry}$) serves as the measuring value. The following is thereby revealed:

a linearity exists between $\gamma$ and r.F.;

the linearity between $\gamma$ and r.F. is present at all temperatures;

the measuring values are reproducible, i.e., they do not change even after several cycles;

the long term behaviour is excellent—i.e., both the specific change in capacitance $\gamma$ as well as the loss angle tan $\delta$ remains constant, and indeed, over a time period of more than 100 days.

What is claimed is:

1. A capacitive moisture sensor with a dielectric comprising a moisture sensitive organic polymer which is mounted between two electrodes, wherein the organic polymer is a polybenzoxazole or a polybenzothiazole.

2. A method for preparing a capacitive moisture sensor comprising the steps of applying a layer or foil of a polybenzoxazole or polybenzothiazole precursor to a first electrically conductive layer, subsequently annealing the layer or foil of precursor such that a layer of polybenzoxazole or polybenzothiazole develops, and providing the resulting benzoxazole or polybenzothiazole layer with a second electrically conductive layer.

3. A method according to claim 2 wherein a photoactive component is added to the polybenzoxazole or polybenzothiazole precursor and wherein the layer or foil of the polymer precursor is photostructured before annealing.

4. A method according to claim 3 wherein the polymer precursor is applied to the first electrically conductive layer as a solution in an organic solvent.

5. A method according to claim 4 wherein N-methylpyrrolidone is used as a solvent.

6. A method according to claim 5 wherein annealing takes place at a temperature from 300° to 500° C.

7. A method according to claim 3 wherein annealing takes place at a temperature from 300° to 500° C.

8. A method according to claim 4 wherein annealing takes place at a temperature from 300° to 500° C.

9. A method according to claim 2 wherein the polymer precursor is applied to the first electrically conductive layer as a solution in an organic solvent.

10. A method according to claim 9 wherein N-methylpyrrolidone is used as a solvent.

11. A method according to claim 10 wherein annealing takes place at a temperature from 300° to 500° C.

12. A method according to claim 9 wherein annealing takes place at a temperature from 300° to 500° C.

13. A method according to claim 2 wherein annealing takes place at a temperature from 300° to 500° C.

* * * * *